United States Patent [19]

Kuhn et al.

[11] Patent Number: 5,254,559
[45] Date of Patent: Oct. 19, 1993

[54] INSECTICIDAL, ACARICIDAL AND MOLLUSCICIDAL 1-(SUBSTITUTED)THIOALKYLPYRROLES

[75] Inventors: David G. Kuhn, Newtown, Pa.; Venkataraman Kameswaran, Princeton Junction, N.J.

[73] Assignee: American Cyanamid Company, Stamford, Conn.

[21] Appl. No.: 804,260

[22] Filed: Dec. 4, 1991

[51] Int. Cl.$^5$ .................. A01N 43/54; A01N 43/76; A01N 43/36; C07D 277/16; C07D 263/58; C07D 403/12; C07D 207/34; C07D 239/10

[52] U.S. Cl. .................. 514/274; 514/369; 514/375; 514/397; 514/422; 514/426; 514/427; 514/387; 548/182; 548/186; 548/189; 548/221; 548/314.7; 548/413; 548/518; 548/558; 548/561; 548/562; 548/306.1; 544/315; 544/316

[58] Field of Search ............... 548/336, 413, 558, 561, 548/562, 518, 314.7, 221, 182, 186, 189, 327; 514/422, 426, 427, 397, 387, 274, 375, 369; 544/315, 316

[56] References Cited

U.S. PATENT DOCUMENTS

| | | | |
|---|---|---|---|
| 4,863,503 | 9/1989 | Anthony et al. | 548/518 |
| 4,929,634 | 5/1990 | Herman et al. | 514/426 |
| 5,010,098 | 4/1991 | Brown et al. | 514/426 |

*Primary Examiner*—Mary C. Lee
*Assistant Examiner*—Joseph K. McKane
*Attorney, Agent, or Firm*—Michael P. Morris

[57] ABSTRACT

There are provided 1-(substituted)thioalkylpyrrole compounds of formula I

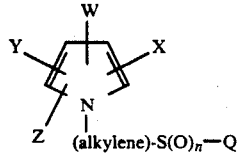

the use thereof for the control of insect, acarid and mollusk pests and methods and compositions for the protection of crops from the ravages of said pests.

28 Claims, No Drawings

INSECTICIDAL, ACARICIDAL AND MOLLUSCICIDAL 1-(SUBSTITUTED)THIOALKYLPYRROLES

BACKGROUND OF THE INVENTION

Pyrrole compounds useful as insecticides, acaricides and molluscicides are described in U.S. Pat. No. 5,010,098 and copending applications Ser. No. 430,601 filed on Nov. 6, 1989, Ser. No. 447,726 filed on Dec. 8, 1989, Ser. No. 522,299 filed on May 11, 1990, Ser. No. 600,054 filed on Oct. 18, 1990 and Ser. No. 795,407 filed on Nov. 20, 1991. However, none of these references disclose pyrrole compounds having a (substituted)thioalkyl moiety on the pyrrole ring nitrogen atom.

Patent applications Ser. Nos. 803,289 and 803,294 filed concurrently herewith describe certain trifluoromethylsulfonylpyrroles useful as insecticidal and fungicidal agents, respectively. However, the pyrrole compounds of the present invention are not described therein. Copending patent application Ser. No. 803,295, filed concurrently herewith describes the fungicidal use of 1-(substituted)thioalkylpyrrole compounds.

SUMMARY OF THE INVENTION

The present invention provides 1-(substituted)thioalkylpyrrole compounds of formula I

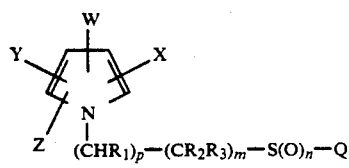

wherein
W is CN or $NO_2$;
X is halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;
Y is $CF_3$, halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;
Z is halogen or $CF_3$;
$R_1$ is hydrogen, $C_1$-$C_6$ or $C_3$-$C_6$cycloalkyl;
$R_2$ and $R_3$ are each independently hydrogen, $C_1$-$C_6$alkyl or $C_3$-$C_6$cycloalkyl;
$R_4$ is hydrogen, fluorine, $CHF_2$, CHFCl or $CF_3$;
$R_5$ is $C_1$-$C_3$alkyl, $C_1$-$C_3$alkoxy or $NR_6R_7$;
$R_6$ is hydrogen or $C_1$-$C_3$alkyl;
$R_7$ is hydrogen, $C_1$-$C_3$alkyl or $R_8CO$;
$R_8$ is hydrogen or $C_1$-$C_3$alkyl;
B is $S(O)_q$ or O;
m, n, p and q are each independently an integer of 0, 1 or 2 with the proviso that the sum (p+m) must be greater than 0;
Q is

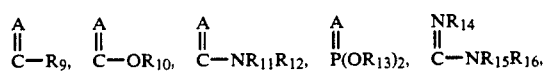

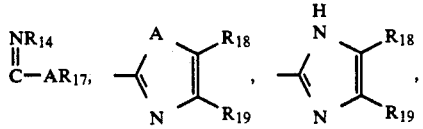

CN, $C_1$-$C_6$ optionally substituted with one or more phenyl, CN or halogen groups or phenyl optionally substituted with one to three $C_1$-$C_3$alkyl, $C_1$-$C_3$alkoxy, halogen, CN, $NO_2$, $CF_3$ or $NR_{20}R_{21}$ groups;
A is O or S;
$R_9$ is $C_1$-$C_6$alkyl or phenyl;
$R_{10}$ is $C_1$-$C_6$alkyl;
$R_{11}$ and $R_{12}$ are each independently hydrogen, $C_1$-$C_6$alkyl or may be taken together with the atom to which they are attached to form a 5- to 7- membered ring;
$R_{13}$ is $C_1$-$C_4$alkyl;
$R_{14}$ is hydrogen, $C_1$-$C_4$alkyl or may be taken together with either $R_{15}$ or $R_{17}$ and the atoms to which they are attached to form a 5- to 7-membered ring optionally substituted with one or two $C_1$-$C_3$alkyl groups;
$R_{15}$ and $R_{16}$ are each independently hydrogen or $C_1$-$C_4$ alkyl;
$R_{17}$ is $C_1$-$C_4$ alkyl or when taken together with $R_{14}$ and the atoms to which they are attached may form a 5- to 7- membered ring optionally substituted with one or two $C_1$-$C_3$alkyl groups;
$R_{18}$ and $R_{19}$ are each independently hydrogen or $C_1$-$C_3$alkyl or when taken together may form a ring wherein $R_{18}R_{19}$ is represented by —CH=CH—CH=CH—;
$R_{20}$ and $R_{21}$ are each independently hydrogen or $C_1$-$C_3$alkyl and
the acid addition salts therof.

There are also provided compositions and methods for the control of insect, acarid and mollusk pests. And, further, a method is provided for the protection of crops, both growing and harvested, from infestation and attack by, said pests.

DETAILED DESCRIPTION OF THE INVENTION

Throughout time, agriculturalists have been seeking effective and efficient means of combatting insect, acarid and mollusk pests. Said pests cause considerable economic damage to essential crops when left unchecked. There is a real need in the art for alternative, effective compounds and compositions useful for agricultural applications as insecticidal, acaricidal and molluscicidal agents.

It is an object of the present invention to provide 1-(substituted)thioalkylpyrrole compounds that are effective agents for the control of insect, acarid, and mollusk pests. It is a further object of this invention to provide methods and compositions for the protection of agronomic crops, both growing and harvested, from the ravages of said pests.

The 1-(substituted)thioalkylpyrrole compounds of the invention have the structural formula I

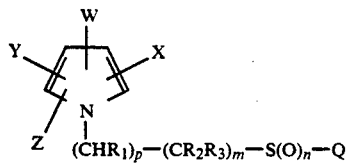

wherein W, X, Y, Z, $R_1$, $R_2$, $R_3$, m, n, p and Q are as described hereinabove. The term halogen, as used in the specification and claims, designates chlorine, fluorine, bromine and iodine. Acid addition salts are those known in the art such as hydrogen halides, hydrogen sulfates, sulfates, sulfonates and the like.

Preferred compounds of the invention are those having structure II

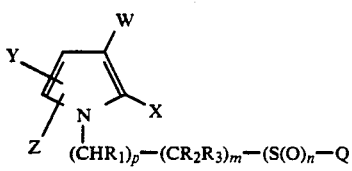

wherein W is CN, n is O and X, Y, Z, $R_1$, $R_2$, $R_3$, m, p and Q are as described hereinabove.

Among the formula II compounds of the present invention which are especially useful for the control of terrestial gastropods such as snails and slugs and aquatic or semi-aquatic mollusks such as cowries and limpets are those wherein W is CN, X, Y and Z are independently halogen or $CF_3$, n and m are 0, p is 1, and Q is as described hereinabove.

Compounds of formula II which are particularly effective insecticidal and acaricidal agents are those wherein W is CN or $NO_2$; X is phenyl optionally substituted with one to three $C_1$-$C_3$alkyl, $C_1$-$C_3$alkoxy, $C_1$-$C_3$alkylthio, halogen or $CF_3$ groups; Y and Z are independently halogen or $CF_3$; n and m are 0, p is 1, and Q is as described hereinabove.

Certain 1-(substituted)thioalkylpyrrole compounds of formula I may be prepared by reacting a pyrrole compound of formula III with a suitable dithiocarbamate, thiocarbamate, thiophosphate or mercaptate alkali metal salt. A specific example of this reaction is illustrated in flow diagram I.

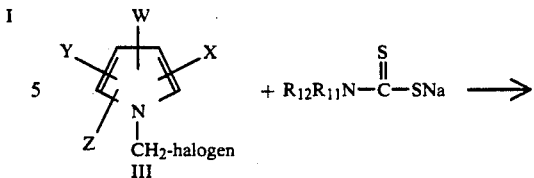

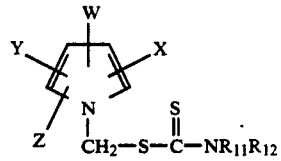

Moreover, certain compounds of formula I may be prepared by reacting the appropriate halomethyl thioether with a pyrrole compound of formula IV in the presence of a base. A representative example is shown in flow diagram II Flow Diagram II

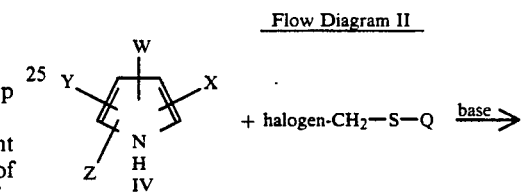

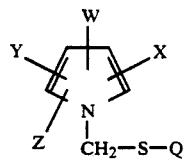

Compounds of formulas III and IV are described in U.S. Pat. No. 5,010,098 and copending patent applications Ser. No. 634,288 filed on Dec. 16, 1990 and Ser. No. 795,407 filed on Nov. 20, 1991 and incorporated herein by reference thereto.

Other compounds of formula I may be prepared by reacting a 1-(halomethyl)pyrrole compound of formula III with a suitable thiourea reagent. In this reaction scheme, the product may be isolated as its acid addition salt. The free base may be obtained using standard procedures such as treatment with excess aqueous base and filtration or extraction of the desired product with a suitable solvent. An illustrative example is shown in flow diagram III.

Flow Diagram III

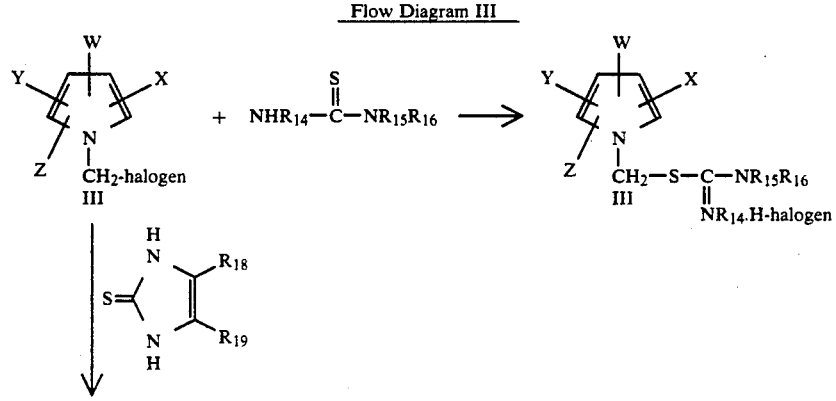

Flow Diagram III

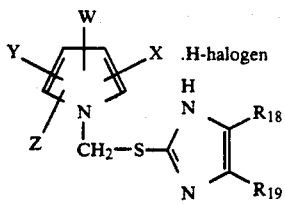

Further compounds of formula I may be prepared by reacting a pyrrole compound of formula IV with a halomethyl compound of formula V wherein $R_1$ is defined hereinabove in the presence of a base such as an alkali metal alkoxide to form the pyrrole intermediate of formula VI. The formula VI intermediate may then be halogenated using conventional halogenating reagents such as N-bromosuccinimide (NBS) to give the desired 1-(haloalkyl)pyrrole second intermediate of formula VII which may then be reacted with an alkali metal thiocarbamate, dithiocarbamate, mercaptate, thiophosphate or the like to yield the 1-(substituted)thioalkylpyrrole product as shown in flow diagram IV.

Flow Diagram IV

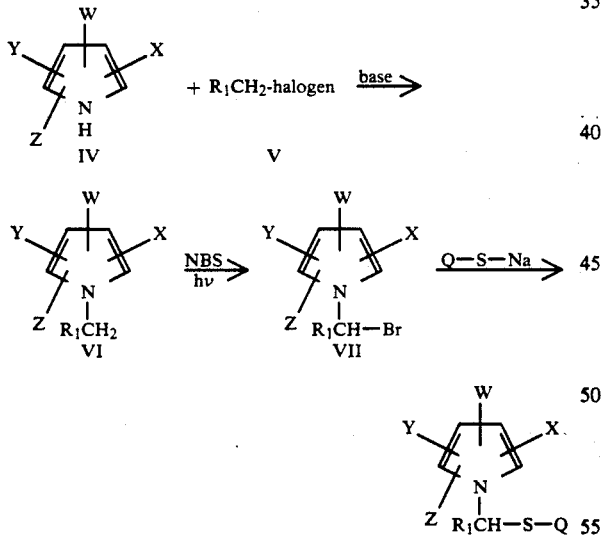

Yet further pyrrole compounds of the invention may be prepared by reacting the formula IV pyrrole with an epoxide of formula VIII in the presence of a base to give the β-hydroxy pyrrole intermediate of formula IX which can then be converted to the corresponding tosylate of formula X by reaction with p-toluenesulfonyl chloride (tsCl) in the presence of an organic base such as pyridine. The tosylate intermediate of formula X may then be reacted with an alkali metal thiocarbamate, dithiocarbamate, mercaptate, thiophosphate or the like to yield the desired 1-(substituted)thioalkylpyrrole product as shown in flow diagram V.

Flow Diagram V

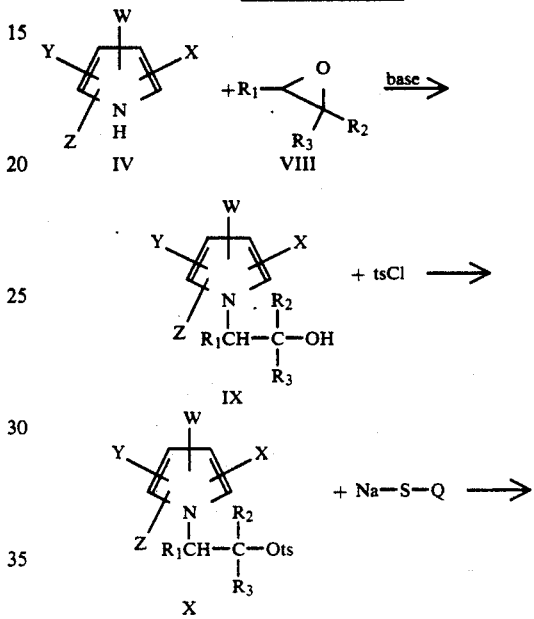

Specific examples are provided below for the purpose of illustration. The examples utilize the above reaction schemes and also provide further means for preparing even more compounds of the invention which are not specifically described hereinabove.

The 1-(substituted)thioalkylpyrrole compounds of the present invention are effective for controlling insect, acarid and mollusk pests. Said pyrroles are also effective for protecting growing or harvested crops from said pests.

In practice, generally about 10 ppm to 10,000 ppm, preferably about 100 to 5,000 ppm, of the formula I compound dispersed in a liquid carrier, when applied to the plants or the soil or water in which the plants are growing, is effective to protect the plants from attack by insects or acarids or mollusks. Compositions of the invention are also effective for protecting turf grass from attack by pests such as grubs, chinch bugs and the like. Applications, such as spray applications, of compositions of the invention are generally effective at rates which provide about 0.125 kg/ha to 4.0 kg/ha of the active 1-(substituted)thioalkylpyrrole compound. Of course, higher rates of application of said pyrrole compounds may be used, if desired.

Advantageously, the compounds of the invention may be used effectively in conjunction with, or in combination with, other biological chemicals, including other insecticides, nematicides, acaricides and mulluscicides such as phosphates, carbamates, pyrethroids, halobenzoylureas, arylpyrroles, nitropyrroles, pyrrole carbonitriles and the like.

A particularly effective method for the control of terrestrial gastropods is to proffer the compound of formula I in a bait formulation. The bait formulation can be widely varied, but in general may contain about 3% to 20% wt/wt, preferably about 5% to 10% wt/wt, of the active ingredient, about 40% to 50% wt/wt of a solid edible substance, about 5% to 10% wt/wt of a carbohydrate source and, the remainder of the formulation, about 30% to 50% of a consumable liquid such as water. The carbohydrate source may be selected from sugar, molasses, corn syrup and the like.

In addition to the above-said bait formulations and spray formulations, the 1-(substituted)thioalkylpyrrole compounds of the present invention may be formulated into granular compositions, flowable compositions, wettable powders, dusts, microemulsions, emulsifiable concentrates and the like. All compositions which lend themselves to soil, water and foliage application and provide effective plant protection are suitable. Compositions of the invention include the formula I compound admixed with an inert solid or liquid carrier.

Where compositions of the invention are to be employed in combination treatments with other pesticidal agents, the composition may be applied as an admixture of the components or may be applied sequentially.

For a more clear understanding of the invention, specific detailed examples of it are set forth below. These examples are merely illustrative, and are not to be understood as limiting the scope and underlying principles of the invention in any way. Unless otherwise noted, all parts are parts by weight. $H^1$NMR and $C^{13}$NMR designate proton nuclear magnetic resonance and carbon 13 nuclear magnetic resonance, respectively.

EXAMPLE 1

Preparation of 4-bromo-2-(p-chlorophenyl)-1-[(imidazol-2-ylthio)methyl]-5-trifluoromethylpyrrole-3-carbonitrile hydrobromide

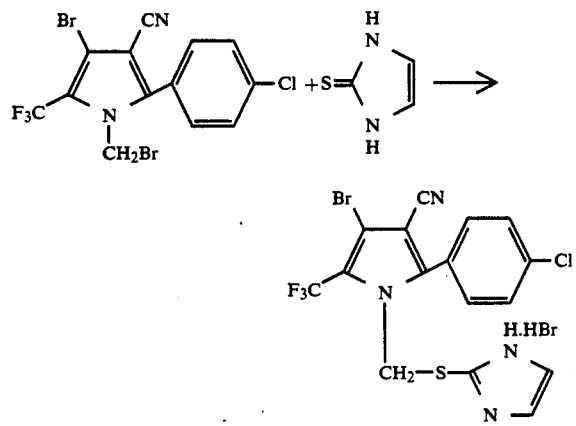

A mixture of 4-bromo-1-(bromomethyl)-2-(p-chlorophenyl)-5-(trifluoromethyl)pyrrole-3-carbonitrile (0.88 g, 0.002 mol) and 4-imidazoline-2-thione (0.23 g, 0.002 mol) in isopropanol is heated at reflux temperature for 3 hours, cooled to room temperature and filtered. The filtercake is washed with isopropanol and air-dried to give the title product as a white solid, 0.81 g (75% yield), mp 221°–223° C.(dec).

EXAMPLES 2–20

Preparation of 1-(substituted)thiomethyl]pyrroles

Using the procedure described in Example 1 and employing the appropriately substituted 1-(halomethyl)pyrrole substrate and a suitable thiourea reagent, the following 1-[(substituted)thiomethyl]pyrrole compounds shown in Table I are obtained.

TABLE I

| Ex. No. | Z | Y | W | X | Q | acid salt | mp °C. |
|---|---|---|---|---|---|---|---|
| 2 | CF$_3$ | Cl | CN | Cl—C$_6$H$_4$— | CH$_3$N, CH$_3$N, H | HCl | 141–144 |
| 3 | CF$_3$ | Cl | CN | Cl—C$_6$H$_4$— | HN, H$_2$N | HCl | 210–213 |
| 4 | CF$_3$ | Cl | CN | Cl—C$_6$H$_4$— | N, N-H | HCl | 189–191 |

TABLE I-continued

[Structure: pyrrole ring with substituents Z, Y, W, X and N-CH₂-S-Q.acid salt]

| Ex. No. | Z | Y | W | X | Q | acid salt | mp °C. |
|---|---|---|---|---|---|---|---|
| 5 | CF₃ | Cl | CN | 4-chlorophenyl | 1,4,5,6-tetrahydropyrimidin-2-yl | HCl | 227–229 |
| 6 | CF₃ | Br | CN | 4-chlorophenyl | 2-methylbenzoxazol-6-yl (with 4-chlorophenyl) | free base | 135–137 |
| 7 | CF₃ | Br | CN | 4-chlorophenyl | 4,5-dihydro-1H-imidazol-2-yl | HBr | 228–230 |
| 8 | CF₃ | Br | CN | 4-chlorophenyl | 1,4,5,6-tetrahydropyrimidin-2-yl | HBr | >225 |
| 9 | CF₃ | Br | CN | 4-chlorophenyl | 1H-benzimidazol-2-yl | HBr | 215–218 (dec) |
| 10 | CF₃ | Br | CN | 4-chlorophenyl | 5,5-dimethyl-1,4,5,6-tetrahydropyrimidin-2-yl | HBr | 224–227 |
| 11 | CF₃ | Br | CN | 4-chlorophenyl | hexahydro-1,3-diazepine-2-thione-2-yl | HBr | 232–234 (dec) |
| 12 | CF₃ | Br | CN | 4-chlorophenyl | C(=NCH₂CH₃)NHCH₂CH₃ | HBr | 128–130 |
| 13 | Br | Br | CN | Br | 1,4,5,6-tetrahydropyrimidin-2-yl | HBr | 215 (dec) |
| 14 | Br | Br | CN | Br | C(=NCH₃)NHCH₃ | HCl | 216 |

TABLE I-continued

Structure:

Y   W
 \\ //
Z—N—X
  |
  CH₂—S—Q·acid salt

| Ex. No. | Z | Y | W | X | Q | acid salt | mp °C. |
|---|---|---|---|---|---|---|---|
| 15 | Cl | Cl | CN | Cl | CH₃N–C(–NHCH₃)– (3,4-dichlorophenyl) | HCl | 180–184 |
| 16 | CF₃ | Br | CN |  | 2-(4-chlorophenyl)-4,5-dihydrothiazol-type | free base | 124.5–125.5 |
| 17 | CF₃ | CF₃ | Br | Cl | tetrahydropyrimidin-2-yl (3,4-dichlorophenyl) | HCl | 225–228 (dec) |
| 18 | CF₃ | CF₃ | Br | Cl | HN=C(NH₂)– (3,4-dichlorophenyl) | HCl | 221 (dec) |
| 19 | Cl | CN | Cl | Cl | CH₃N–C(–NHCH₃)– (3,4-dichlorophenyl) | HCl | 194–197 |
| 20 | Br | Br | CN | Br | HN=C(NH₂)– | HCl | 225 (dec) |

Ex. No. designates Example Number

EXAMPLE 21

Preparation of [3-Chloro-5-(p-chlorophenyl)-4-cyano-2-(trifluoromethyl)pyrrole-1-yl]dimethyldithiocarbamic acid, methyl ester

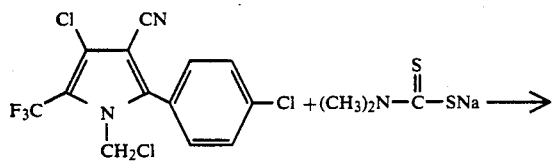

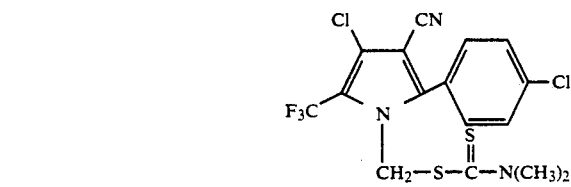

A mixture of 4-chloro-1-(chloromethyl)-2-(p-chlorophenyl)-5-(trifluoromethyl)pyrrole-3-carbonitrile (0.7 g, 0.002 mol) and dimethyldithiocarbamic acid, sodium salt (0.57 g, 0.004 mol) in dimethyl formamide is heated at 50°–55° for 30 minutes, cooled to room temperature and poured into water. The resultant mixture is extracted with ethyl acetate. The combined extracts are washed with a saturated sodium chloride solution, dried (MgSO₄) and concentrated in vacuo to give an orange oil residue. The residue is mixed with hot hexane, cooled and filtered to give an orange solid filtercake. Recrystallization of the solid from isopropanol gives the title product as a tan crystaline solid, 0.7 g (80% yield), mp 129°–131° C.

EXAMPLES 22–43

Preparation of (substituted pyrrole-1-yl)dithiocarbamate, thiocarbamate and thiophosphate methyl esters and thioalkyl derivatives Using the procedure described in Example 21 and employing the appropriately substituted 1-halo methylpyrrole and the sodium salt of the desired dithiocarbamate, thiocarbamate, thiophosphate or mercaptate reagent the following compounds shown in Table II are obtained.

TABLE II

[Structure: pyrrole ring with Z and X at 2,5-positions, Y and W at 3,4-positions, N-substituent CH₂-S-Q]

| Ex. No. | Z | Y | W | X | Q | mp °C. |
|---|---|---|---|---|---|---|
| 22 | $CF_3$ | Cl | CN | 4-Cl-C₆H₄ | $(CH_3)_2CHOC(=S)-$ | 94–95 |
| 23 | $CF_3$ | Cl | CN | 4-Cl-C₆H₄ | $CH_3CH_2OC(=S)-$ | (oil) |
| 24 | $CF_3$ | Br | CN | 4-Cl-C₆H₄ | $(CH_3)_2NC(=S)-$ | 125–128 |
| 25 | $CF_3$ | Br | CN | 4-Cl-C₆H₄ | $CH_3$ | |
| 26 | $CF_3$ | Br | CN | 4-Cl-C₆H₄ | $(CH_3CH_2)_2NC(=S)-$ | 101–103 |
| 27 | $CF_3$ | Br | CN | 4-Cl-C₆H₄ | $[(CH_3)_2CHO]_2P(=S)-$ | 108–110 |
| 28 | Cl | Cl | CN | 3,4-Cl₂-C₆H₃ | $CH_3CH_2OC(=S)-$ | 82–85 |
| 29 | $CF_3$ | Br | CN | 4-Cl-C₆H₄ | $CH_3CH_2OC(=S)-$ | 85–86 |
| 30 | $CF_3$ | Br | CN | 4-Cl-C₆H₄ | $(CH_3)_2CHOC(=S)-$ | 120–121.5 |
| 31 | Br | Br | CN | Br | $(CH_3)_2NC(=S)-$ | 170–172 |
| 32 | Cl | Cl | CN | 3,4-Cl₂-C₆H₃ | $(CH_3)_2NC(=S)-$ | 194–197 |

TABLE II-continued

[Structure: pyrrole ring with substituents Y (top-left), W (top-right), Z (bottom-left), X (bottom-right), N at bottom with CH₂—S—Q substituent]

| Ex. No. | Z | Y | W | X | Q | mp °C. |
|---|---|---|---|---|---|---|
| 33 | $CF_3$ | $CF_3$ | Br | 3,4-dichlorophenyl | $(CH_3)_2NC(=S)-$ | 128–129 |
| 34 | Br | Br | CN | Br | $CH_3C(=O)-$ | 135–137 |
| 35 | $CF_3$ | $CF_3$ | Br | 3,4-dichlorophenyl | $CH_3CH_2OC(=S)-$ | (oil) |
| 36 | Cl | CN | Cl | 3,4-dichlorophenyl | $(CH_3)_2NC(=S)-$ | 120–123 |
| 37 | Cl | CN | Cl | 3,4-dichlorophenyl | $CH_3CH_2OC(=S)-$ | 100–105 |
| 38 | Br | Br | CN | Br | CN | 168–170 |
| 39 | Br | Br | CN | phenyl-$CH_2S-$ | phenyl-$CH_2-$ | 50–53 |
| 40 | Br | Br | CN | Br | phenyl-$CH_2-$ | 106–110.5 |
| 41 | $CF_3$ | Br | CN | 4-chlorophenyl | pyrrolidinyl-$N-C(=S)-$ | 106–110 |
| 42 | $CF_3$ | Br | CN | 4-chlorophenyl | CN | 95–97 |
| 43 | Br | Br | CN | $CH_3S-$ | $CH_3-$ | 110–111 |

Ex. No. designates Example Number

EXAMPLE 14

Preparation of
4,5-dibromo-1-[(methylthio)methyl]-2-(α,α,α-trifluoro-p-tolyl)pyrrole-3-carbonitrile

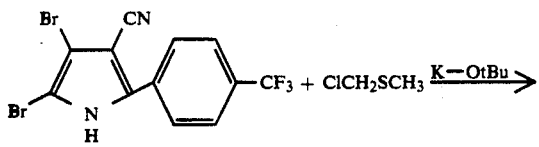

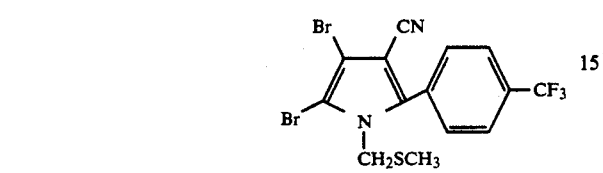

A solution of 4,5-dibromo-2-(α,α,α-trifluoro-p-tolyl)-pyrrole-3-carbonitrile (0.56 g, 1.42 mmol) in dry tetrahydrofuran, under nitrogen, is treated portion-wise with potassium t-butoxide (0.21 g, 1.81 mmol), stirred at 25° C. for ¾ hour, treated dropwise with chloromethyl methyl thioether (0.18 g, 1.81 mmol), stirred at room temperature for 16 hours, heated at 49°-60° C. until reaction is complete by thin layer chromatography. The reaction mixture is diluted with water and ether. The phases are separated and the organic layer is dried over MgSO4 and concentrated in vacuo to give a black oil residue. The residue is flash chromatographed (silica/ 100:100:1 ether:petroleum ether:ethyl acetate) to give the title product as a red solid, mp 140°-145° C., identified by H$^1$NMR and mass spectral analyses.

EXAMPLE 45

Preparation of
4,5-dibromo-1[(phenylthio)methyl]-2-(α,α,α-trifluoro-p-tolyl)pyrrole-3-carbonitrile

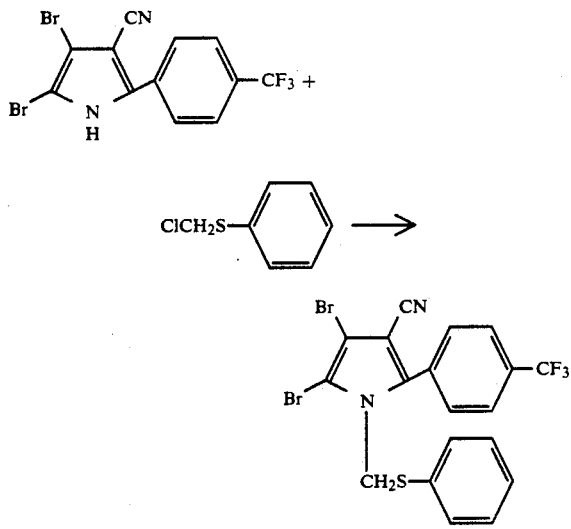

Following the procedure described in Example 44, above, and substituting chloromethyl phenyl thioether as the alkylating reagent, the title product is obtained as a red oil, bp>200° C./0.7 mmHg, identified by H$^1$NMR, C$^{13}$NMR and mass spectral analyses.

EXAMPLE 46

Preparation of
4-bromo-2-(p-chlorophenyl)-1-[(phenyl-sulfonyl)methyl]-5-trifluoromethyl)pyrrole-3-carbonitrile

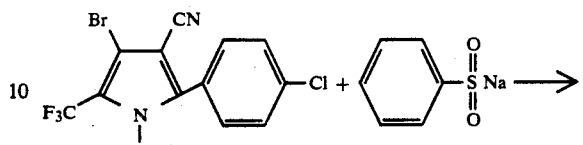

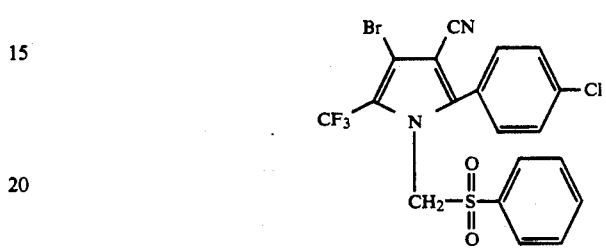

A stirred solution of 4-bromo-1-(bromomethyl)-2-(p-chlorophenyl)-5-(trifluoromethyl)pyrrole-3-carbonitrile (0.65 g, 1.5 mmol) in dry dimethyl formamide is treated with sodium benzylsulfonate (0.485 g, 3.0 mmol), heated at 70° C. for 3 hours, cooled to room temperature and diluted with a mixture of water and ethyl acetate. The organic phase is separated, dried over MgSO4 and concentrated in vacuo to give a yellow oil residue. Column chromatography (silica gel/4:1 hexanes:ethyl acetate) gives the title product as a white solid, mp 165°-166.5° C., identified by H$^1$NMR and mass spectral analyses.

EXAMPLE 47

Insecticidal and acaricidal evaluations of test compounds

Test solutions are prepared by dissolving the test compound in a 35% acetone in water mixture to give a concentration of 10,000 ppm. Subsequent dilutions are made with water as needed.

*Heliothis virescens*, egg, tobacco budworm

A young cotton leaf about 6-7 cm in length is dipped in an agitated test suspension for about 3 seconds. Eggs are collected on a cheesecloth and the cloth is cut into 10-20mm squares, each containing approximately 50-100 eggs which are 6-30 hours old. The egg-containing cheesecloth square is similarly dipped in a test suspension and placed on a treated cotton leaf. The combination is dried in a hood and then placed in an 8 ounce Dixie ® cup #2168-ST (240 ml volume, 6 cm tall, 9.5 cm top diameter, 8.0 cm bottom diameter) into which a 5 cm length of damp dental wick has been placed. The cup is covered with a clear plastic lid and held for 3 days, after which mortality counts are made.

*Heliothis virescens*, 3rd instar tobacco budworm

Cotton cotyledons are dipped in the test solution and allowed to dry in a hood. When dry, each is cut into quarters and ten sections are placed individually in 30 mL plastic medicine cups containing a 5-7 mm long piece of damp dental wick. One 3rd instar caterpillar is added to each cup and the cup is sealed with MYLAR film. Treatments are maintained for 3 days before a mortality count and observation of reduction in feeding damage are made.

*Spodoptera eridania,* 3rd instar larvae, southern armyworm

A Sieva limabean leaf expanded to 7–8 cm in length is dipped in the test solution with agitation for 3 seconds and allowed to dry in a hood. The leaf is then placed in a 100×10 mm petri dish containing a damp filterpaper on the bottom and ten 3rd instar caterpillars. At 3 and 5 days, observations are made of mortality, reduced feeding, or any interference with normal molting.

*Spodoptera eridania,* 3rd instar larvae, southern armyworm, 7-day residual

The limabean leaves treated in the above test are maintained under high intensity lamps in the greenhouse for 7 days. These lamps duplicate the effects of a bright sunny day in June in New Jersey and are kept on for 14 hour day length. After 7 days, the foliage is sampled and assayed as in the above-said test.

*Spodoptera eridania,* systemic uptake, 3rd instar larvae, southern armyworm

An emulsion containing 0.1 gm of the test compound, 0.2 gm of Emulphor EL-620® emulsifier, 10 mL of acetone and 90 mL of water is prepared and diluted 10-fold with water to give a 100 ppm emulsion. Subsequent 10-fold dilutions are made with water as needed. Sieva limabean plants, with the primary leaves expanded to a length of 7–8 cm, are cut off at least 3 cm above the soil level to avoid contamination with soil bacteria which will cause decay of the stem during the test. The cut stem is placed in the test emulsion and wrapped with a bit of cotton to hold the stem off the bottom of the bottle and to limit evaporation. The treated stem is thus maintained for 3 days at 27° C. to allow the test compound to be taken up into the plant. Following this, one leaf is removed from the plant and placed in a 100×10 mm petri dish with 10 southern armyworms as described above. Mortality counts and observations of feeding damage are made 3 and 5 days later.

*Diabrotic undecimpunctata howardi,* 3rd instar southern corn rootworm

One cc of fine talc is placed in a 30 mL wide-mouth screw-top glass jar. One mL of the appropriate acetone test solution is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 6 days when mortality counts are made. Missing larvae are presumed dead, since they decompose rapidly and can not be found. The concentrations used in this test correspond approximately to 50 and 10 kg/ha, respectively.

*Tetranychus urticae* (OP-resistant strain), 2-spotted spider mite

Sieva limabean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant and to lay eggs. The size of the cut, infested leaf is varied to obtain about 100 mites per leaf. At the time of test treatment, the piece of leaf used to transfer the mites is removed and discarded. The newly mite-infested plants are dipped in the test solution for 3 seconds with agitation and set in the hood to dry. After 2 days one leaf is removed and mortality counts are made. After 5 days, another leaf is removed and observations are made of mortality of the eggs and/or newly emerged nymphs.

*Aphis fabae,* mixed instar, bean aphid

Pots containing single nasturtium plants (Tropaeolum sp.) about 5 cm tall are infested with about 100–200 aphids one day prior to treatment. Each pot is sprayed with the test solution for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and mortality estimates are made after 2 days.

*Empoasca abrupta,* adult, western potato leafhopper

A Sieva limabean leaf about 5 cm long is dipped in the test solution for 3 seconds with agitation and placed in a hood to dry. The treated leaf is placed in a 100×10 mm petri dish containing a moist filter paper and about 10 adult leafhoppers are added. After 2 days, mortality counts are made.

*Empoasca abrupta,* adult, western potato leafhopper Systemic Uptake

An emulsion containing 0.1 gm of the test material, 0.2 gm of Emulphor EL-620® emulsifier, 10 mL of acetone and 90 mL of water is prepared and diluted 10-fold with water to give a 100 ppm emulsion. Subsequent 10-fold dilutions are made with water as needed. Sieva limabean plants, with the primary leaves expanded to a length of 7–8 cm, are cut off at least 3 cm above the soil level to avoid contamination with soil bacteria which will cause decay of the stem during the test. The cut stem is placed in the test emulsion and wrapped with a bit of cotton to hold the stem off the bottom of the bottle and to limit evaporation. The treated stem is maintained for 3 days at 27° C. to allow the test compound to be taken up into the plant. Following this, one leaf is removed from the plant and placed in a 100×10 mm petri dish containing a moist filter paper and about 10 adult leafhoppers as described above. Mortality counts are made after 2 days.

All of the above tests are rated according to the rating scale shown below.

Rating Scale:

| | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

The data obtained are shown in Tables III and IV wherein the test compounds are identifed by Example Number.

TABLE III

Insecticidal And Acaricidal Evaluation Of Test Compounds

| Compound (Ex. No.) | TOBACCO BUDWORM ||||||| ARMYWORM |||||||||| SOUTHERN CORN ROOTWORM (ppm) |||
|---|---|---|---|---|---|---|---|---|---|---|---|---|---|---|---|---|---|---|
| | Egg (ppm) ||| 3rd Instar (ppm) ||| Day 3 (ppm) |||| Day 5 (ppm) |||| Stem Sys (ppm) | | | |
| | 1000 | 300 | 100 | 1000 | 100 | 10 | 1000 | 100 | 10 | R | 1000 | 100 | 10 | R | 1000 | 50 | 10 | 1 |
| 44 | 0 | — | — | 9 | 0 | 0 | 9 | 9 | 0 | 0 | 9 | 9 | 0 | 2 | 0 | 3 | 0 | — |
| 45 | 0 | — | — | 0 | 0 | — | 8 | 0 | — | 0 | 8 | 0 | — | 0 | 0 | 0 | — | — |
| 2 | 0 | — | 0 | 9 | 9 | 9 | 9 | 9 | 9 | 9 | 9 | 9 | 9 | 9 | 0 | 8 | 0 | 0 |
| 3 | 5 | — | 0 | 9 | 9 | 8 | 9 | 9 | 8 | — | 9 | 9 | 9 | — | 0 | 9 | 0 | 0 |
| 22 | 0 | — | — | 9 | 9 | 3 | 9 | 9 | 9 | — | 9 | 9 | 9 | — | 0 | 9 | 8 | 3 |
| 23 | 0 | — | — | 9 | 9 | 5 | 9 | 9 | 9 | — | 9 | 9 | 9 | — | — | 9 | 6 | 0 |
| 4 | 9 | — | 9 | 9 | 9 | 9 | 9 | 9 | 9 | 9 | 9 | 9 | 9 | 9 | 0 | 0 | — | — |
| 25 | 0 | — | — | 9 | 9 | 8 | 9 | 9 | 0 | 9 | 9 | 9 | 0 | 9 | 0 | 0 | 0 | — |
| 5 | 0 | — | — | 9 | 9 | 0 | 9 | 9 | 4 | 9 | 9 | 9 | 4 | 9 | 8 | 0 | — | — |
| 21 | 0 | — | 0 | 9 | 9 | 9 | 9 | 9 | 9 | 9 | 9 | 9 | 9 | 9 | 0 | 9 | 0 | 0 |
| 24 | 0 | — | — | 9 | 9 | 0 | 9 | 9 | 9 | 9 | 9 | 9 | 9 | 9 | 0 | 9 | 0 | 0 |
| 46 | 0 | — | — | 9 | 4 | — | 9 | 0 | 0 | 4 | 9 | 0 | 0 | 9 | 0 | 8 | 0 | 0 |
| 6 | 0 | — | — | 9 | 8 | 0 | 9 | 9 | 0 | 9 | 9 | 9 | 5 | 9 | 0 | 9 | 5 | 0 |
| 7 | 9 | 8 | 0 | 9 | 9 | 5 | 9 | 9 | 9 | 9 | 9 | 9 | 9 | 9 | 0 | 9 | 0 | 0 |
| 8 | 0 | — | 0 | 9 | 9 | 3 | 9 | 9 | 0 | 9 | 9 | 9 | 6 | 9 | 9 | 0 | — | — |
| 9 | 0 | — | — | 0 | 0 | — | 6 | 0 | — | 9 | 7 | 0 | — | 9 | 0 | 0 | — | — |
| 10 | 0 | — | 0 | 9 | 8 | 0 | 9 | 9 | 0 | 9 | 9 | 9 | 0 | 9 | 0 | 0 | — | — |
| 11 | 5 | — | 3 | 9 | 9 | 6 | 9 | 9 | 9 | 9 | 9 | 9 | 9 | 9 | 9 | 0 | — | — |
| 12 | 0 | — | — | 9 | 9 | 8 | 9 | 9 | 9 | 9 | 9 | 9 | 9 | 9 | 0 | 8 | 9 | 0 |
| 26 | 0 | — | — | 9 | 9 | 9 | 9 | 9 | 9 | 9 | 9 | 9 | 9 | 9 | 0 | 9 | 4 | 0 |
| 27 | 0 | — | — | 9 | 7 | 0 | 9 | 9 | 0 | 9 | 9 | 9 | 0 | 9 | 0 | 9 | 7 | 6 |
| 1 | 0 | — | 0 | 9 | 9 | 4 | 9 | 9 | 9 | 9 | 9 | 9 | 9 | 9 | 0 | 0 | — | — |
| 28 | 0 | — | 0 | 9 | 3 | 0 | 9 | 9 | 6 | 9 | 9 | 9 | 6 | 9 | 0 | 0 | — | — |
| 29 | 4 | — | 0 | 9 | 9 | 4 | 9 | 9 | 9 | 9 | 9 | 9 | 9 | 9 | 0 | 9 | — | — |
| 30 | 0 | — | 0 | 9 | 9 | 4 | 9 | 9 | 9 | 9 | 9 | 9 | 9 | 9 | 0 | 9 | — | — |
| 13 | 0 | — | — | 0 | — | — | 9 | 0 | — | 0 | 9 | 3 | — | 7 | 7 | 0 | — | — |
| 31 | 0 | — | — | 6 | — | — | 9 | 9 | 0 | 9 | 9 | 9 | 0 | 9 | 0 | 0 | — | — |
| 14 | 0 | — | — | 8 | 0 | — | 9 | 9 | 0 | 0 | 9 | 9 | 0 | 5 | 0 | 0 | — | — |
| 15 | 0 | — | 0 | 9 | 6 | 0 | 9 | 9 | 9 | 9 | 9 | 9 | 9 | 9 | 0 | 0 | — | — |
| 32 | 0 | — | — | 0 | 0 | — | 9 | 3 | 0 | 0 | 9 | 3 | 0 | 0 | 0 | 0 | — | — |
| 16 | 0 | — | 0 | 9 | 9 | 9 | 9 | 9 | 9 | 9 | 9 | 9 | 9 | 9 | 4 | 9 | — | — |
| 17 | 0 | — | — | 9 | 8 | 8 | 9 | 9 | 9 | 9 | 9 | 9 | 9 | 9 | 0 | 7 | — | — |
| 18 | 0 | — | — | 9 | 9 | 0 | 9 | 9 | 0 | 9 | 9 | 9 | 0 | 9 | 0 | 0 | — | — |
| 33 | 0 | — | — | 9 | 9 | 7 | 9 | 9 | 9 | 9 | 9 | 9 | 9 | 9 | 0 | — | — | — |
| 43 | 0 | — | — | 0 | — | — | 9 | 0 | 0 | * | 9 | 0 | 0 | * | 0 | 0 | — | — |
| 34 | 8 | — | — | 9 | 0 | — | 9 | 9 | 5 | * | 9 | 9 | 5 | * | 0 | 0 | — | — |
| 35 | 0 | — | — | 9 | 9 | 8 | 9 | 9 | 9 | 9 | 9 | 9 | 9 | 9 | 0 | 0 | — | — |
| 36 | 0 | — | — | 9 | 9 | 0 | 9 | 9 | 8 | 9 | 9 | 9 | 8 | 9 | 0 | 0 | — | — |
| 19 | 0 | — | — | 9 | 9 | 0 | 9 | 9 | 0 | 9 | 9 | 9 | 0 | 9 | 0 | 0 | — | — |
| 37 | 0 | — | — | 9 | 9 | 0 | 9 | 9 | 9 | 9 | 9 | 9 | 9 | 9 | 0 | 0 | — | — |
| 38 | — | — | — | — | — | — | 9 | — | — | — | 9 | — | — | — | — | 0 | — | — |
| 20 | 0 | 0 | 0 | 9 | 0 | 0 | 9 | 9 | 0 | 6 | 9 | 9 | 0 | * | — | 0 | — | — |
| 40 | 0 | — | — | 0 | 0 | — | 9 | 0 | 0 | 0 | 9 | 0 | 0 | * | 0 | 0 | — | — |

R designates Residual
Stem Sys designates Stem Systemic

TABLE IV

Insecticidal And Acaricidal Evaluation Of Test Compounds

| Compound (Ex. No.) | OP-RESISTANT MITES ||||||||| APHIDS (ppm) | LEAFHOPPER |||
|---|---|---|---|---|---|---|---|---|---|---|---|---|---|
| | Adult (ppm) ||| Egg (ppm) ||| Nymph (ppm) ||| | Contact (ppm) || Systemic (ppm) |
| | 300 | 100 | 10 | 300 | 100 | 10 | 300 | 100 | 10 | 100 | 100 | 10 | 100 |
| 44 | 9 | 7 | 0 | 0 | 7 | 0 | 8 | 0 | 5 | 0 | 7 | 0 | 0 |
| 2 | 9 | 9 | 8 | 0 | 9 | 0 | 9 | — | 7 | 0 | 9 | 8 | 0 |
| 3 | 4 | 9 | 8 | 4 | 9 | 1 | 9 | — | 0 | 0 | 9 | 9 | 0 |
| 22 | 9 | 9 | 9 | 0 | 9 | 9 | 9 | — | — | 7 | 9 | 9 | 0 |
| 23 | 9 | 9 | 9 | 0 | 9 | 9 | 9 | — | — | 5 | 9 | 9 | 0 |
| 4 | 9 | 6 | 0 | 9 | 0 | 0 | — | 0 | 0 | 0 | 9 | 0 | 0 |
| 25 | 7 | — | — | 0 | — | — | 0 | — | — | 0 | 9 | 0 | 0 |
| 5 | 9 | 8 | 0 | 0 | 9 | 0 | 0 | — | 0 | 0 | 9 | 4 | 8 |
| 21 | 9 | 9 | 9 | 0 | 8 | 0 | 9 | 0 | 0 | 0 | 9 | 5 | 0 |
| 24 | 0 | 9 | 9 | 9 | 9 | 0 | — | — | 0 | 7 | 9 | 0 | 0 |
| 7 | 9 | 9 | 9 | 0 | 9 | 0 | 0 | — | 0 | 0 | 9 | 5 | 0 |
| 8 | 9 | 9 | 0 | 0 | 8 | 4 | 0 | 8 | 0 | 0 | 8 | 0 | — |
| 10 | 0 | — | — | 0 | — | — | 0 | — | — | 0 | 7 | 0 | 6 |
| 11 | 0 | — | — | 0 | — | — | 0 | — | — | 0 | 9 | 8 | 9 |
| 12 | 0 | — | — | 0 | — | — | 0 | — | — | 0 | 9 | 5 | — |
| 1 | 0 | — | — | 0 | — | — | 0 | — | — | 0 | 9 | 7 | 0 |
| 28 | 9 | 9 | 3 | 0 | 9 | 0 | 0 | — | 3 | 0 | 9 | 0 | 0 |
| 29 | 9 | 9 | 9 | 0 | 9 | 9 | 0 | — | — | 0 | 9 | 9 | 0 |
| 30 | 9 | 9 | 9 | 0 | 9 | 9 | 0 | — | — | 3 | 9 | 8 | 0 |
| 13 | 5 | — | — | 0 | — | — | 0 | — | — | 0 | 0 | — | 0 |

TABLE IV-continued

Insecticidal And Acaricidal Evaluation Of Test Compounds

| Compound (Ex. No.) | OP-RESISTANT MITES ||||||||| APHIDS (ppm) | LEAFHOPPER |||
|---|---|---|---|---|---|---|---|---|---|---|---|---|---|
| | Adult (ppm) ||| Egg (ppm) ||| Nymph (ppm) ||| | Contact (ppm) || Systemic (ppm) |
| | 300 | 100 | 10 | 300 | 100 | 10 | 300 | 100 | 10 | 100 | 100 | 10 | 100 |
| 14 | 0 | — | — | 0 | — | — | 0 | — | — | 0 | 0 | — | 7 |
| 15 | 0 | — | — | 0 | — | — | 0 | — | — | 0 | 6 | 0 | 0 |
| 16 | 0 | — | — | 0 | — | — | 0 | — | — | 8 | 9 | 9 | 0 |
| 17 | 7 | 0 | 0 | 0 | 7 | 0 | 0 | 0 | 0 | 0 | 5 | — | 0 |
| 18 | 9 | 9 | 0 | 0 | 0 | 0 | 0 | 0 | 0 | 0 | 9 | 4 | 0 |
| 33 | 7 | 0 | 0 | 0 | 8 | 0 | 0 | 0 | 0 | 0 | 8 | 0 | 0 |
| 34 | 0 | — | — | 0 | — | — | 0 | — | — | 8 | 0 | — | 0 |
| 35 | 9 | 9 | 8 | 0 | 9 | 3 | 0 | — | 0 | 0 | 9 | 9 | 0 |
| 36 | 7 | 0 | 0 | 0 | 0 | 0 | 0 | 0 | 0 | 0 | 6 | — | 0 |
| 19 | 5 | — | — | 0 | — | — | 0 | — | — | 0 | 9 | 0 | 0 |
| 37 | 7 | 9 | 0 | 0 | 9 | 2 | 0 | — | 4 | 0 | 6 | — | 0 |

We claim:

1. A compound having the structure

I

[structure with W, X, Y, Z substituents on a ring with N, and $(CHR_1)_p-(CR_2R_3)_m-S(O)_n-Q$]

wherein

W is CN or $NO_2$;

X is halogen or phenyl optionally substituted with one to three $C_1-C_3$alkyl, $C_1-C_3$alkoxy, $C_1-C_3$alkylthio, $C_1-C_3$alkylsulfinyl, $C_1-C_3$alkylsulfonyl, halogen, CN, $NO_2$, $CF_3$, $R_4CF_2B$, $R_5CO$ or $NR_6R_7$ groups;

Y is $CF_3$, halogen or phenyl optionally substituted with one to three $C_1-C_3$alkyl, $C_1-C_3$alkoxy, $C_1-C_3$alkylthio, $C_1-C_3$alkylsulfinyl, $C_1-C_3$alkylsulfonyl, halogen, CN, $NO_2$, $CF_3$, $R_4CF_2B$, $R_5CO$ or $NR_6R_7$ groups;

Z is halogen or $CF_3$;

$R_1$ is hydrogen, C or $C_3-C_6$cycloalkyl;

$R_2$ and $R_3$ are each independently hydrogen, $C_1-C_6$ or $C_3-C_6$cycloalkyl $R_4$ is hydrogen, fluorine, $CHF_2$, $CHFCl$ or $CF_3$;

$R_5$ is $C_1-C_3$alkyl, $C_1-C_3$alkoxy or $NR_6R_7$;

$R_6$ is hydrogen or $C_1-C_3$alkyl;

$R_7$ is hydrogen, $C_1-C_3$alkyl or $R_8CO$;

$R_8$ is hydrogen or $C_1-C_3$alkyl; B is $S(O)_q$ or O;

m, n, p and q are each independently an integer of 0, 1 or 2 with the proviso that the sum (p+m) must be greater than 0;

Q is $$\overset{A}{\underset{\|}{C}}-R_9, \quad \overset{A}{\underset{\|}{C}}-OR_{10}, \quad \overset{A}{\underset{\|}{C}}-NR_{11}R_{12}, \quad \overset{A}{\underset{\|}{P}}(OR_{13})_2, \quad \overset{NR_{14}}{\underset{\|}{C}}-NR_{15}R_{16},$$

$$\overset{NR_{14}}{\underset{\|}{C}}-AR_{17}, \quad \text{[pyridine ring with } A, R_{18}, R_{19}\text{]}, \quad \text{[pyridine ring with } H, N, R_{18}, R_{19}\text{]},$$

CN, $C_1-C_6$alkyl optionally substituted with one or more phenyl, CN or halogen groups or phenyl optionally substituted with one to three $C_1-C_3$alkyl, $C_1-C_3$alkoxy, halogen, CN, $NO_2$, $CF_3$ or $NR_{20}R_{21}$ groups;

A is O or S;

$R_9$ is $C_1-C_6$alkyl or phenyl;

$R_{10}$ is $C_1-C_6$alkyl;

$R_{11}$ and $R_{12}$ are each independently hydrogen, $C_1-C_6$alkyl or may be taken together with the atom to which they are attached to form a 5- to 7- membered ring;

$R_{13}$ is $C_1-C_4$alkyl;

$R_{14}$ is hydrogen, $C_1-C_4$alkyl or may be taken together with either $R_{15}$ or $R_{17}$ and the atoms to which they are attached to form a 5- to 7-membered ring optionally substituted with one or two $C_1-C_3$alkyl groups;

$R_{15}$ and $R_{16}$ are each independently hydrogen or $C_1-C_4$alkyl;

$R_{17}$ is $C_1-C_4$alkyl or when taken together with $R_{14}$ and the atoms to which they are attached may form a 5- to 7- membered ring optionally substituted with one or two $C_1-C_3$alkyl groups;

$R_{18}$ and $R_{19}$ are each independently hydrogen or $C_1-C_3$alkyl or when taken together may form a ring wherein $R_{18}R_{19}$ is represented by $-CH=CH-CH=CH-$;

$R_{20}$ and $R_{21}$ are each independently hydrogen or $C_1-C_3$alkyl and the acid addition salts therof.

2. The compound according to claim 1 having the structure

[structure with W, X, Y, Z, N, $R_1-CH-S(O)_n-Q$]

3. The compound according to claim 1 wherein W is CN; X is halogen or phenyl optionally substituted with one to three halogen, CN or $CF_3$ groups; Y and Z are each independently halogen or $CF_3$; n and m are 0; and p is 1.

4. The compound according to claim 1 wherein Q is

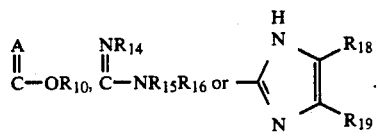

5. The compound according to claim 2 wherein W is CN; X is halogen or phenyl optionally substituted with one to three halogen, CN or CF$_3$ groups; Y and Z are each independently halogen or CF$_3$ and n is 0.

6. The compound according to claim 5 wherein Q is

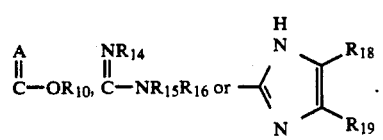

7. The compound according to claim 6 wherein R$_1$ is hydrogen.

8. The compound according to claim 7 wherein R$_{10}$ is C$_1$–C$_6$ alkyl, R$_{14}$, R$_{15}$ and R$_{16}$ are each independently hydrogen, C$_1$–C$_4$ alkyl or R$_{14}$ and R$_{15}$ may be taken together with the atoms to which they are attached to form a 5- or 6-membered ring and R$_{18}$ and R$_{19}$ are each independently hydrogen or C$_1$–C$_3$ alkyl.

9. The compound according to claim 1, 2-{[3-chloro-5-(p-chlorophenyl)-4-cyano-2-(trifluoromethyl)pyrrol-1-yl]methyl}-2-thio-pseudourea.

10. The compound according to claim 1, S-[3-chloro-5-(p-chlorophenyl)-4-cyano-2-(trifluoromethyl)pyrrol-1-yl]methyldithiocarbonic acid, O-isopropyl ester.

11. The compound according to claim 1, S-[3-chloro-5-(p-chlorophenyl)-4-cyano-2-(trifluoromethyl)pyrrol-1-yl]methyldithiocarbonic acid, O-ethyl ester.

12. The compound according to claim 1, 2-{[3-chloro-5-(p-chlorophenyl)-4-cyano-2-(trifluoromethyl)-pyrrol-1-yl]methyl}-1,3-dimethyl-2-thio-pseudourea.

13. The compound according to claim 1, 4-chloro-2-(p-chlorophenyl)-1-[(2-imidazolin-2-ylthio)methyl]-5-(trifluoromethyl)pyrrole-3-carbonitrile.

14. The compound according to claim 1, 4-chloro-2-(p-chlorophenyl)-1-{[(1,4,5,6-tetrahydro-2-pyrimidinyl)thio]methyl}-5-(trifluoromethyl)pyrrole-3-carbonitrile.

15. The compound according to claim 1, [3-bromo-5-(p-chlorophenyl)-4-cyano-2-(trifluoromethyl)pyrrol-1-yl]dimethylthiocarbamic acid, methyl ester.

16. The compound according to claim 1, 4-bromo-2-(p-chlorophenyl)-1-[(2-imidazolin-2-ylthio)methyl]-5-(trifluoromethyl)pyrrole-3-carbonitrile.

17. The compound according to claim 1, S-[3-bromo-5-(p-chlorophenyl)-4-cyano-2-(trifluoromethyl)pyrrol-1-yl]methyl dithiocarbonic acid, O-ethyl ester.

18. The compound according to claim 1, S-[3-bromo-5-(p-chlorophenyl)-4-cyano-2-(trifluoromethyl)pyrrol-1-yl]methyl dithiocarbonic acid, O-isopropyl ester.

19. A method for the control of insect, acarid or mollusk pests which comprises contacting said pests or their food supply, habitat or breeding grounds with a pesticidally effective amount of a compound having the structure

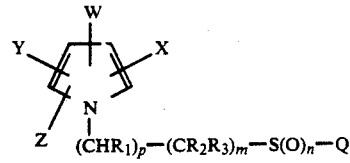

wherein W, X, Y, Z, R$_1$, R$_2$, R$_3$, m, n, p, and Q are described in claim 1.

20. The method according to claim 19 wherein the compound has the structure

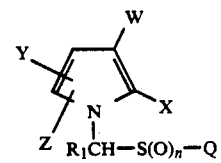

21. The method according to claim 20 wherein W is CN; X is halogen or phenyl optionally substituted with one to three halogen, CN or CF$_3$ groups; Y and Z are each independently halogen or CF$_3$ and n is O.

22. The method according to claim 21 wherein Q is

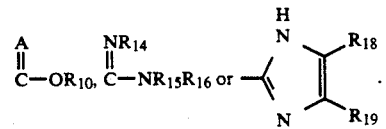

23. The method according to claim 19 wherein the compound is selected from the group consisting of
2-{[3-chloro-5-(p-chlorophenyl)-4-cyano-2-(trifluoromethyl)pyrrol-1-yl]methyl}-2-thio-pseudourea;
S-[3-chloro-5-(p-chlorophenyl)-4-cyano-2-(trifluoromethyl)pyrrol-1-yl]methyldithiocarbonic acid, O-isopropyl ester;
S-[3-chloro-5-(p-chlorophenyl)-4-cyano-2-(trifluoromethyl)pyrrol-1-yl]methyldithiocarbonic acid, O-ethyl ester;
2-{[3-chloro-5-(p-chlorophenyl)-4-cyano-2-(trifluoromethyl)pyrrol-1-yl]methyl]-1,3-dimethyl-2-thio-pseudourea;
4-chloro-2-(p-chlorophenyl)-1-[(2-imidazolin-2-ylthio)methyl]-5-(trifluoromethyl)-pyrrole-3-carbonitrile;
4-chloro-2-(p-chlorophenyl)-1-{[(1,4,5,6-tetrahydro-2pyrimidinyl)thio]methyl}-5-(trifluoromethyl)pyrrole-3-carbonitrile;
[3-bromo-5-(p-chlorophenyl)-4-cyano-2-(trifluoromethyl)pyrrol-1-yl]dimethylthiocarbamic acid, methyl ester;
4-bromo-2-(p-chlorophenyl)-1-[(2-imidazolin-2-ylthio)methyl]-5-(trifluoromethyl)pyrrole-3-carbonitrile;
S-[3-bromo-5-(p-chlorophenyl)-4-cyano-2-(trifluoromethyl)pyrrol-1-yl]methyl dithiocarbonic acid, O-ethyl ester and
S-[3-bromo-5-(p-chlorophenyl)-4-cyano-2-(trifluoromethyl)pyrrol-1-yl]methyl dithiocarbonic acid, O-isopropyl ester.

24. A method for the protection of growing plants from attack or infestation by insect, acarid or mollusk pests which comprises applying to the foliage of said plants, or to the soil or water in which they are growing, a pesticidally effective amount of a compound having the structure

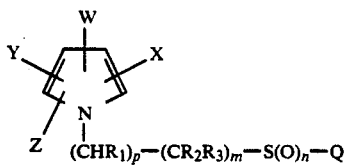

wherein W, X, Y, Z, R₁, R₂, R₃, m, n, p and Q are described in claim 1.

25. The method according to claim 24 wherein the compound has the structure

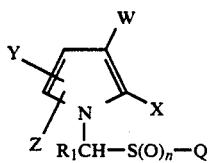

26. The method according to claim 25 wherein W is CN; X is halogen or phenyl optionally substituted with one to three halogen, CN or CF₃ groups; X and Y are each independently halogen or CF₃; n is O and Q is

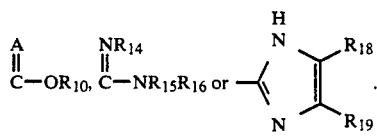

27. The method according to claim 24 wherein the compound is selected from the group consisting of 2-{[3-chloro-5-(p-chlorophenyl)-4-cyano-2-(trifluoromethyl)pyrrol-1-yl]methyl}-2-thio-pseudourea;

S-[3-chloro-5-(p-chlorophenyl)-4-cyano-2-(trifluoromethyl)pyrrol-1-yl]methyldithiocarbonic acid, O-isopropyl ester;

S-[3-chloro-5-(p-chlorophenyl)-4-cyano-2-(trifluoromethyl)pyrrol-1-yl]methyldithiocarbonic acid, O-ethyl ester;

2-{[3-chloro-5-(p-chlorophenyl)-4-cyano-2-(trifluoromethyl)pyrrol-1-yl]methyl}-1,3-dimethyl-2-thio-pseudourea;

4-chloro-2-(p-chlorophenyl)-1-[(2-imidazolin-2-ylthio)methyl]-5-(trifluoromethyl)pyrrole-3-carbonitrile;

4-chloro-2-(p-chlorophenyl)-1-{[(1,4,5,6-tetrahydro-2-pyrimidinyl)thio]methyl}-5-(trifluoromethyl)pyrrole-3-carbonitrile;

[3-bromo-5-(p-chlorophenyl)-4-cyano-2-(trifluoromethyl)pyrrol-1-yl]dimethylthiocarbamic acid, methyl ester;

4-bromo-2-(p-chlorophenyl)-1-[(2-imidazolin-2-ylthio)methyl]-5-(trifluoromethyl)pyrrole-3-carbonitrile;

S-[3-bromo-5-(p-chlorophenyl)-4-cyano-2-(trifluoromethyl)pyrrol-1-yl]methyl dithiocarbonic acid, O-ethyl ester and S-[3-bromo-5-(p-chlorophenyl)-4-cyano-2-(trifluoromethyl)pyrrol-1-yl]methyl dithiocarbonic acid, O-isopropyl ester.

28. A composition for controlling insect, acarid or mollusk pests which comprises an inert liquid or solid carrier and a pesticidally effective amount of a compound having the structure

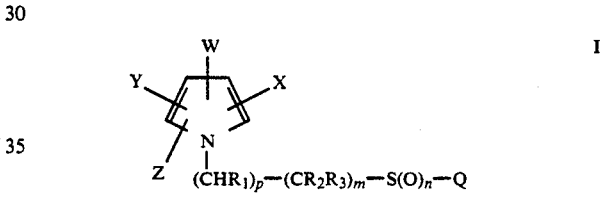

wherein W, X, Y, Z, R₁, R₂, R₃, m, n, and p and Q are as described in claim 1.

* * * * *

UNITED STATES PATENT AND TRADEMARK OFFICE
CERTIFICATE OF CORRECTION

PATENT NO. : 5,254,559
DATED : October 19, 1993
INVENTOR(S) : David G. Kuhn, et al It is certified that error appears in the above-indentified patent and that said Letters Patent is hereby corrected as shown below:

Column 23, Claim 1, line 42, should read:

--$R_1$ is hydrogen, $C_1$-$C_3$alkyl or $C_3$-$C_6$cycloalkyl;--

Claim 1, line 43 should read:

--$R_2$ and $R_3$ are each independently hydrogen, $C_1$-$C_6$alkyl or $C_3$-$C_6$cycloalkyl--

Signed and Sealed this

Tenth Day of May, 1994

Attest:

BRUCE LEHMAN

Attesting Officer          Commissioner of Patents and Trademarks